United States Patent [19]

Su

[11] Patent Number: 4,774,336

[45] Date of Patent: Sep. 27, 1988

[54] PROCESS FOR PREPARING N-SUBSTITUTED PIPERAZINES FROM ETHYLENE GLYCOL AND AMINES

[75] Inventor: Wei-Yang Su, Austin, Tex.

[73] Assignee: Texaco Inc., White Plains, N.Y.

[21] Appl. No.: 914,224

[22] Filed: Oct. 2, 1986

[51] Int. Cl.$^4$ .......................................... C07D 295/02
[52] U.S. Cl. ................................ 544/404; 544/358; 544/392; 544/395
[58] Field of Search .............. 544/404, 392, 395, 358

[56] References Cited

U.S. PATENT DOCUMENTS

| | | | |
|---|---|---|---|
| 3,029,240 | 4/1962 | Erner | 544/404 |
| 3,037,025 | 5/1962 | Godfrey | 544/404 |
| 3,067,199 | 12/1962 | Langdon | 544/410 |
| 3,120,524 | 2/1964 | Godfrey | 544/404 |
| 3,647,795 | 3/1972 | Bluestein et al. | 544/404 |
| 3,697,524 | 10/1972 | Tomalia et al. | 544/404 |
| 3,907,802 | 9/1975 | Demmering | 544/404 |
| 4,123,462 | 10/1978 | Best | 544/358 |
| 4,709,034 | 11/1987 | Marsella | 544/358 |

FOREIGN PATENT DOCUMENTS 234401 9/1987 European Pat. Off. .

OTHER PUBLICATIONS

Tsuji et al., Tetrahedron Letters, vol. 27, No. 3, pp. 377–380 (1986).
Watanabe et al., J. Org. Chem., 1984, 49, 3359–3363.
Tsuji et al., J. Org. Chem., 1985, 50, 1365–1370.

*Primary Examiner*—Donald G. Daus
*Assistant Examiner*—Cecilia Shen
*Attorney, Agent, or Firm*—Jack H. Park; Kenneth R. Priem; Cynthia L. Kendrick

[57] ABSTRACT

N,N'-dialkylpiperazines are prepared by contacting ethylene glycol and a primary amine in the presence of a homogeneous ruthenium-phosphine catalyst. For example, ethylene glycol and aniline are reacted in the presence of ruthenium trichloride and triphenylphosphine to produce N,N'-diphenylpiperazine.

9 Claims, No Drawings

PROCESS FOR PREPARING N-SUBSTITUTED PIPERAZINES FROM ETHYLENE GLYCOL AND AMINES

FIELD OF THE INVENTION

This invention concerns a one-step process for preparation of N-substituted piperazines. More particularly this invention relates to the preparation of N-substituted piperazines from ethylene glycol and primary amines in the presence of a homogeneous ruthenium-phosphine catalyst under mild conditions.

BACKGROUND OF THE INVENTION

The preparation of piperazines and various derivatives thereof by cyclization reactions, some of which are vapor phase processes is known in the art. Generally speaking processes known for the manufacture of N,N'-disubstituted piperazines have been characterized by one or more disadvantages such as requiring expensive starting materials or requiring high pressure reaction conditions, or obtaining low yields. The preparation of N-substituted piperazines from inexpensive starting materials in good yields and at mild conditions does not appear previously taught.

The process set forth in U.S. Pat. No. 3,067,199 discloses the use of alkanolamines heated in the presence of a nickel or cobalt hydrogenation/dehydrogenation catalyst to produce alkyl-substituted piperazines and alkyl-substituted pyrazines.

One of the earlier patents in this area teaches the preparation of dimethylpiperazine by subjecting the vapors of a compound from the group consisting of a methylated tetraethylenepentamine or a lower methylated linear member (monomer, dimer or trimer) of the ethylene diamine family to a silica-alumina cracking catalyst at a temperature of about 600°–700° F. (See U.S. Pat. No. 3,029,240)

In U.S. Pat. No. 3,037,025 a method of producing N-alkyl-substituted piperazines is revealed which permits a broad choice of raw materials to be used and allows the production of a relatively high proportion of the valuable N-monosubstituted piperazines as compared to the preparation of N,N'-disubstituted piperazines. The reactant compound is represented by the formula:

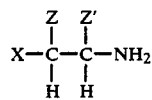

wherein Z and Z' are selected from the group consisting of hydrogen and lower alkyl radicals. X represents a radical selected from the group consisting of OH, NH$_2$ and

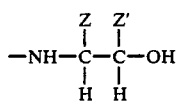

in which Z and Z' have the values noted above, with an alkanol represented by the formula ROH in which R is an alkyl radical. This compound is reacted in the presence of hydrogen and a hydrogenation catalyst. In this reference, with the temperature around 250° C., the best yield of N,N'-dimethylpiperazine was about 16%.

In U.S. Pat. No. 3,120,524 N-monoalkyl-substituted piperazines are prepared in one step by contacting an amine with a hydrogenation catalyst in the presence of hydrogen at a temperature around 250° C., said amine being represented by the formula:

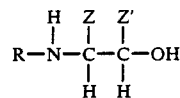

wherein R represents a lower alkyl radical and Z and Z' are selected from the group consisting of hydrogen and a lower alkyl. The yield of N,N'-disubstituted piperazines was under 10%.

U.S. Pat. Nos. 3,037,025 and 3,120,524 describe techniques where low yields of N,N'-dialkylpiperazines are obtained using temperatures in the range of 250° C. and pressures close to 500 psig.

U.S. Pat. No. 3,647,795 discloses a process for cyclodehydration of N-substituted ethanolamine to produce N,N'-disubstituted piperazine by passing the vapors of said N-substituted ethanolamine over an activated alumina catalyst at high temperatures of 500°–700° F. The ability to selectively cyclohydrate N-substituted ethanolamines at atmospheric pressure was a novel feature. The yields of N,N'-dialkylpiperazines range from 30–70%.

U.S. Pat. No. 3,067,199 relates to a method for preparing alkyl-substituted piperazines and alkyl-substituted pyrazines with high conversions and high yields by heating an alkanolamine in the presence of a nickel or cobalt hydrogenation/dehydrogenation catalyst. The preferred temperature range was 130°–240° C. and the preferred pressure range was 200–1200 psig. The yields were as high as 70–85%.

Tomalia et al. disclose a process for preparing 1,4-disubstituted piperazines by contacting a basic catalytic aziridine with sulfur dioxide in the presence of a catalytic amount of iodide ion. (See U.S. Pat. No. 3,697,524)

In Tetrahedron Letters, Vol. 27, No. 3, pp. 377–380, 1986, Watanabe discloses the reaction of N-methylaniline with ethylene glycol in the presence of a homogeneous ruthenium catalyst to provide a 51% yield of 1-methylindole. He also reported that:

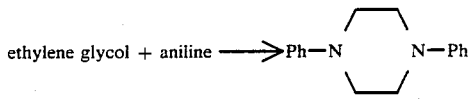

In many of the references found in the art the substituted piperazines are formed by reacting vapors at high pressures and temperatures. None of the references found used common, inexpensive reactants to make N,N'-disubstituted piperazines. In most of the reactions, mild conditions were not sufficient to bring about good yields.

It would be an advance in the art if N-substituted piperazines could be prepared in good conversion and yield under mild conditions from relatively inexpensive starting materials.

SUMMARY OF THE INVENTION

This invention concerns a method for making N-substituted piperazines as exemplified by N,N'-di-t-butylpiperazine, N,N'-dipropylpiperazine, N,N'-diisopropylpiperazine, N,N'-dimethylpiperazine and N,N'-diphenylpiperazine which comprises contacting a mixture of ethylene glycol with various primary amines in the presence of a homogeneous catalyst comprising a ruthenium-containing compound and a phosphine compound in a solvent at a temperature of at least 100° C. and a pressure of at least 50 psi.

Most N-substituted piperazines are known to be useful as acid scavengers and urethane catalysts.

DETAILED DESCRIPTION

In the narrower and more preferred practice of this invention, N-substituted piperazines are prepared from a vicinal glycol and a primary amine by a process comprising:

(a) Contacting said mixture of vicinal glycol, most often ethylene glycol, and primary amine with a catalyst system comprising a homogeneous ruthenium-phosphine catalyst and a solvent, (b) heating said reaction mixture to a temperature of at least 100° C. and a pressure of at least 50 psig and (c) separating said N,N'-disubstituted piperazines contained therein.

The reaction of ethylene glycol with primary amines to form N,N'-disubstituted piperazines can be represented by the equation:

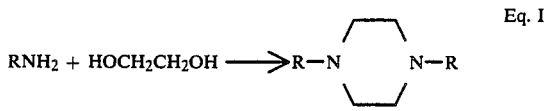

Eq. I

In order to present the inventive concept in the greatest possible detail to promote its understanding, the following supplementary disclosure is submitted. The basic invention improved upon here is practiced as follows:

Catalysts which are suitable in the practice of this invention contain ruthenium. The ruthenium-containing catalyst may be chosen from a wide variety of organic or inorganic compounds, complexes, etc. It is only necessary that the catalyst precursor actually employed contain said metal in any of its ionic states. The actual catalytically active species is then believed to comprise ruthenium and excess phosphine in complex combination with ethylene glycol and a primary amine in a solvent. The most effective catalyst is believed to be achieved where a ruthenium salt of a mineral acid is mixed with a trialkylphosphine ligand in a solvent under reaction conditions.

The ruthenium catalyst precursors may take many different forms. For instance, the ruthenium may be added to the reaction mixture in an oxide form, as in the case of, for example, ruthenium(IV) oxide hydrate. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, such as, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydridocarbonyl derivative. Here, suitable examples include triruthenium dodecacarbonyl and other hydridocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include ruthenium salts of a mineral acid. Among these, particularly preferred is ruthenium trichloride.

The preferred catalyst comprises a ruthenium source plus a tertiary phosphine such as a trialkyl phosphine or a triarylphosphine such as triphenylphosphine. A preferred example is ruthenium trichloride in the presence of an excess of tributylphosphine.

Suitable tertiary phosphine components comprising the preferred catalyst formulations may contain one or more trivalent phosphorus atoms per molecule, bonded to alkyl, aryl, alkaryl and aralkyl radicals, or mixtures thereof. Specific examples of such tertiary phosphines include tri-n-butylphosphine, tri-sec-butylphosphine, trimethylphosphine, triethylphosphine, tri-c-hexylphosphine, triphenylphosphine, tri-p-tolylphosphine, benzyldiphenylphosphine, tri-p-methoxyphenylphosphine, as well as 1,2-bis(dibenzylphosphino)ethane
1,2-bis(di-n-butylphosphino)ethane
1,2-bis(dicyclohexylphosphino)ethane
1,2-bis(diethylphosphino)ethane
1,2-bis(dimethylphosphino)ethane
1,4-bis(diphenylphosphino)butane
1,2-bis(diphenylphosphino)ethane
1,6-bis(diphenylphosphino)hexane
1,5-bis(diphenylphosphino)pentane
1,3-bis(diphenylphosphino)propane
1,2-bis(di-n-propylphosphino)ethane
n-butydiphenylphosphine
diethylphenylphosphine
di-n-hexylphenylphosphine
ethyldiphenylphosphine
hexyldiphenylphosphine
tribenzylphosphine, triisobutylphosphine,
tri-n-propylphosphine As mentioned above the preferred reactants are a vicinal glycol and an amine. Vicinal glycol which will work in the process of the invention is ethylene glycol.

Suitable nitrogen-containing coreactants useful in the practice of this invention include primary amines containing one to 12 carbon atoms. These amines may be straight or branched chain aliphatic series, they may be cycloaliphatic amines, or they may be aromatic amines. Examples of suitable primary aliphatic amines include methylamine, ethylamine, isopropylamine, tert-butylamine, n-propylamine, n-hexylamine and n-dodecylamine. Aryl primary amines include aniline.

Suitable solvents include polar solvents such as ethers. 1,4-dioxane, methyl tertiary butyl ether, methyl tertiary amyl ether tetraglyme and tetrahydrofuran will work. Also suitable are tertiary amides, such as dimethyl formamide and dimethyl sulfoxide. The preferred solvent was 1,4-dioxane.

The quantity of ruthenium compound, phosphine compound and solvent employed in the instant invention is not critical and may vary over a wide range. In general, the novel process is desirably conducted in the presence of a catalytically effective quantity of active ruthenium species, phosphine compound and solvent which gives the desired product in reasonable yield. The reaction proceeds when employing as little as about $1 \times 10^{-6}$ weight percent and even lesser amounts of ruthenium.

The upper concentration is dictated by a variety of factors including catalyst cost, operating temperature, etc. A ruthenium concentration of from about 0.0001 to about 1 weight percent in conjunction with a phosphine concentration of from about 0.001 to about 10 weight percent and a solvent concentration of from 0 to about 70 based on the total weight of the reaction mixture is desirable in the practice of this invention.

The temperature range which can usefully be employed in these syntheses is a variable dependent upon other experimental factors, including the pressure, the concentration and the choice of the particular species of ruthenium catalyst, among other things. The range of operability is from about 100° to 300° C. A narrow range of 150°–250° C. represents the preferred temperature range.

Superatmospheric pressures of 50 psi or greater lead to substantial yields of N,N'-disubstituted piperazines by the process of this invention. A preferred operating range is above 50 psi. The most preferred range is from 100–300 psi, but pressures greater than 300 psi can be used.

The novel process of this invention can be conducted in a batch, semi-continuous or continuous fashion and said material may be recovered by methods well known in the art, such as distillation, fractionation, extraction and the like.

The major products of these syntheses are N,N'-disubstituted piperazines, particularly N,N'-disubstituted piperazines such as N,N'-di-t-butylpiperazine, N,N'-di-propylpiperazine, N,N'-diisopropylpiperazine, N,N'-dimethylpiperazine and N,N'-diphenylpiperazine. The principal by-products of these preparations are N-alkylmonoethanolamine, N-alkyl-bis-(2-hydroxyethyl)amine and N,N'-dialkyl-N-ethanolethylenediamine.

The products have been identified in this work by one or more of the following analytical procedures, viz, gas-liquid phase chromatography (glc), infrared (ir), mass spectrometry, proton nuclear magnetic resonance (H'-nmr) and elemental analyses, or a combination of these techniques. All temperatures are in degrees centigrade and all pressures are in pounds per square inch gauge (psig).

Having described the inventive process, the following examples are submitted to supply specific and illustrative embodiments.

EXAMPLE 1

A 300-ml stirred autoclave with pyrex liner was charged with a mixture of t-butylamine (19.7 g, 0.27 mol), ethylene glycol (16.7 g, 0.27 mol), tributylphosphine (2.3 ml), ruthenium trichloride (0.736 g) and 1,4-dioxane (40 ml). The reactor was sealed and purged of air. The reaction was heated to 180° C. and held for five hours. During the process, the pressure went up to 200 psi. The reaction was allowed to cool to room temperature. After GC analysis which showed no ethylene glycol left, the solvent was removed at reduced pressure. The residue was sublimated at 40°–50° C. under the vacuum to yield 14.7 g of N,N'-di-t-butylpiperazine (55% yield).

EXAMPLE 2

Ethylene glycol (24.8 g, 0.40 ml), n-propylamine (23.6 g, 0.40 mol), RuCl$_3$nH$_2$O(0.521 g), Bu$_3$P (1.6 ml), and 1,4-dioxane (30 ml) were subjected to a reaction as described in Example 1 above. The products were distilled to obtain a 51% yield of N,N'-di-propylpiperazine with a 100% conversion of ethylene glycol.

EXAMPLE 3

Ethylene glycol (13.3 g, 0.21 mol) and isopropylamine (12.4 g, 0.21 mol) were subjected to a reaction as described above. A 50% yield of N,N'-diisopropylpiperazine was obtained with a 100% conversion of ethylene glycol.

EXAMPLE 4

Ethylene glycol (11.0 g, 0.18 mol) and methylamine (5.5 g, 0.18 mol) were subjected to a reaction as described above, except that the reaction temperature was 150° C. A 27% yield of N,N'-dimethylpiperazine was obtained with a 32% conversion of ethylene glycol.

EXAMPLE 5

Ethylene glycol (15.6 g, 0.25 mol), aniline (23.3 g, 0.25 mol), RuCl$_3$ nH$_2$O (0.518 g), Ph$_3$P (1.66 g) and 1,4-dioxane (25 ml) were subjected to a reaction as described above, except that the reaction temperature was 185° C. There was essentially complete conversion of ethylene glycol with an approximately 80% yield of the N,N'-diphenylpiperazine.

What is claimed is:

1. A process for preparing N,N'-di-t-butylpiperazine by reacting ethylene glycol and tert-butylamine in the presence of a homogeneous catalyst comprising ruthenium trichloride hydrate and tributylphosphine in the presence of a solvent from the group consisting of aliphatic and heterocyclic ethers at a temperature of 150° C. to 250° C. and a pressure of 100 psi to 300 psi.

2. The process of claim 1 wherein the ruthenium-containing compound is ruthenium trichloride hydrate.

3. The process of claim 1 wherein the phosphine-containing compound is a triarylphosphine selected from the group including tri-n-butylphosphine and triphenylphosphine.

4. The process of claim 1 wherein the temperature is from 150°–250° C.

5. The process of claim 1 wherein the pressure is from 100 psi to 300 psi.

6. The process of claim 1 further comprising conducting the desired synthesis of N-substituted piperazines in the presence of a solvent.

7. The process of claim 6 wherein the solvent is 1,4-dioxane.

8. A process for preparing N,N'-dipropylpiperazine by reacting ethylene glycol and n-propylamine in the presence of a homogeneous catalyst comprising ruthenium trichloride hydrate and tributylphosphine at a temperature of 150° C. to 250° C. and a pressure of 100 psi to 300 psi.

9. A process for preparing N,N'-diisopropylpiperazine by reacting ethylene glycol and isopropylamine in the presence of a homogeneous catalyst comprising ruthenium trichloride hydrate and tributylphosphine at a temperature of 150° C. to 250° C. and a pressure of 100 psi to 300 psi.

* * * * *